US005783742A

United States Patent [19]

Shibamoto et al.

[11] Patent Number: 5,783,742

[45] Date of Patent: Jul. 21, 1998

[54] METHOD OF INJECTING A SAMPLE INTO GAS CHROMATOGRAPH

[75] Inventors: Shigeaki Shibamoto; Masahito Ueda, both of Kyoto, Japan

[73] Assignee: Shimadzu Corporation, Kyoto, Japan

[21] Appl. No.: 749,197

[22] Filed: Nov. 14, 1996

[30] Foreign Application Priority Data

Nov. 27, 1995 [JP] Japan .................................... 7-332828

[51] Int. Cl.[6] ........................................................ G01N 1/00

[52] U.S. Cl. .................... 73/23.41; 73/864.86; 73/864.87

[58] Field of Search ................................ 73/23.41, 23.42, 73/23.35, 863.11, 863.12, 864.81, 864.83, 826.87; 422/81

[56] References Cited

U.S. PATENT DOCUMENTS 4,289,029 9/1981 Sampson et al. .................... 73/863.11
4,615,226 10/1986 DiNuzzo et al. .................... 73/863.11
5,037,611 8/1991 Ledford, Jr. .............................. 422/81
5,150,601 9/1992 Simeroth et al. ...................... 73/23.41
5,472,670 12/1995 Harrington et al. .................. 73/23.41

*Primary Examiner*—Hezron E. Williams
*Assistant Examiner*—Nashmiya Ashraf
*Attorney, Agent, or Firm*—Keiichi Nishimura

[57] ABSTRACT

A sample is injected into a gas chromatograph by first slowly causing a needle of a syringe containing the sample to penetrate a septum and be inserted into a sample vaporization chamber and then quickly pushing a plunger to inject the sample into the sample vaporization chamber and pulling out the needle out of the sample vaporization chamber such that effects of discrimination can be controlled and the stress on the needle can be reduced.

2 Claims, 1 Drawing Sheet

3
2
6
12
4
10
14

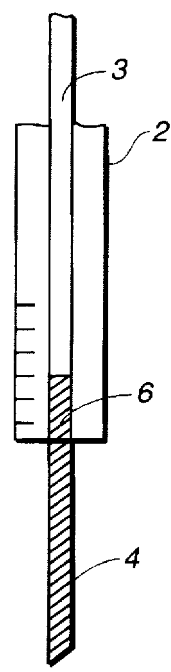
FIG._1A
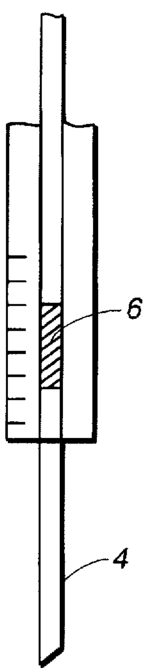
FIG._1B
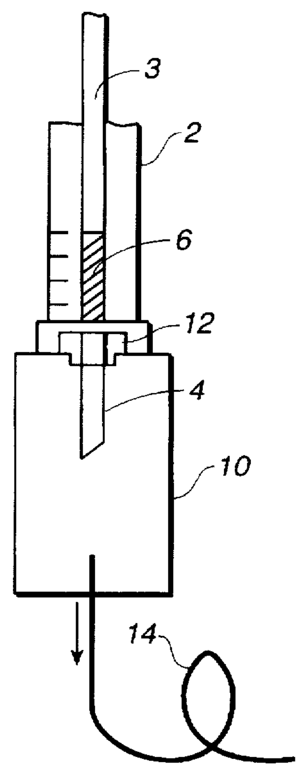
FIG._1C
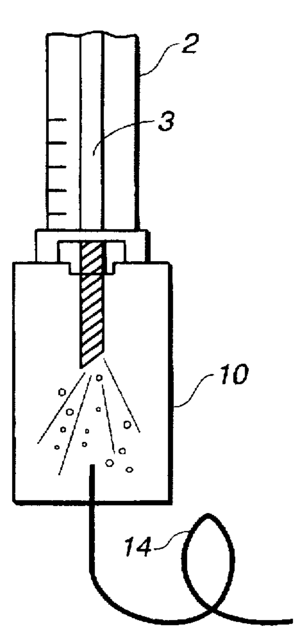
FIG._1D
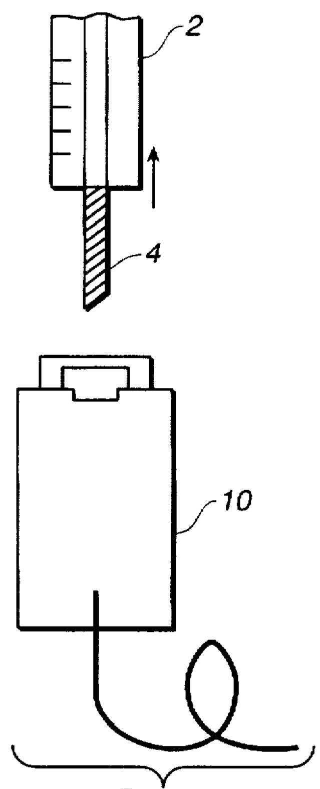
FIG._1E

METHOD OF INJECTING A SAMPLE INTO GAS CHROMATOGRAPH

BACKGROUND OF THE INVENTION

This invention relates to a method of injecting a sample into a gas chromatograph and more particularly to a method comprising a first process of causing a needle of a syringe to penetrate a septum and be inserted into a sample vaporization chamber of a gas chromatograph either for a simple substance or of a gas chromatograph-mass spectrometer combination after an auto-injector may be used to have the sample introduced into the syringe, a second process of thereafter pushing a plunger of this syringe to inject the sample into the sample vaporization chamber and a third process of further thereafter pulling the needle of the syringe out of the sample vaporization chamber.

When a liquid sample is introduced into a gas chromatograph, the temperature of the sample vaporization chamber is kept higher than the vaporization temperature of the target component to be measured. The sample is injected through the needle of a syringe into the vaporization chamber and vaporized, and the sample thus vaporized is introduced into the column by means of a carrier gas. After the sample is injected into the vaporization chamber by pushing the plunger of the syringe, a portion of the sample remains in the needle of the syringe. Since the sample vaporization chamber is heated and at a high temperature, the needle also becomes hot, and the components with low boiling points in the sample remaining inside the needle are vaporized and enter the sample vaporization chamber. This phenomenon is referred to as "discrimination". When discrimination takes place, the composition of the sample injected for analysis is affected, and the result of the analysis is not accurate any more.

In order to prevent such a change in the composition due to discrimination, it has been proposed in Japanese Patent Publication Tokkai 61-178658 to carry out quickly all three of the processes of inserting the needle of the syringe into the sample vaporization chamber, pushing the plunger to inject the sample into the sample vaporization chamber and pulling the needle of the syringe from the sample vaporization chamber such that this series of processes can be completed in less than 500 milliseconds.

The shorter the time required to complete the series of processes for injecting the sample, the smaller will be the effect of change in composition due to discrimination. Of the three processes described above, if the process of inserting the needle of the syringe into the sample vaporization chamber through a septum is carried out too speedily, however, the instantaneous increase in stress on the tip of the needle becomes very large when the needle penetrates the septum, thereby increasing the probability of causing the needle to be bent and giving rise to the maintenance problem of frequently exchanging the needles.

SUMMARY OF THE INVENTION

It is therefore an object of this invention to provide an improved method of injecting a sample into a gas chromatograph by preventing the change in composition of the sample due to discrimination at the time of the injection and reducing stress on the tip of the needle of the syringe such that the probability of bending the needle will be lowered.

According to a method embodying this invention, the process of inserting the needle of the syringe through the septum of the sample vaporization chamber is carried out relatively slowly over a period of over 400 milliseconds, but the processes of pushing the plunger to inject the sample into the sample vaporization chamber and pulling the needle of the syringe out of the sample vaporization chamber are carried out sufficiently faster than the first process of inserting the syringe needle into the septum such that they can be completed in less than 200 milliseconds.

In summary, not all of the series of processes are required to be carried out equally quickly, but the effect of change in composition due to discrimination can be controlled by carrying out sufficiently quickly the process of injecting the sample after the syringe needle has been inserted into the sample vaporization chamber as well as the process thereafter of retracting the syringe needle from the sample vaporization chamber. Since the process of causing the syringe needle to penetrate the septum and enter the sample vaporization chamber is carried out sufficiently slowly, the load on the driving means for driving the syringe is reduced, and the instantaneous stress on the tip of the needle is dispersed, thereby reducing the probability of bending the needle. As a result, the useful lifetime of the syringe needle can be extended.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIGS. 1A–1E are schematic sectional views of a sample injector for a gas chromatograph for showing the steps in a method of sample injection embodying this invention.

DETAILED DESCRIPTION OF THE INVENTION

When a liquid sample is analyzed by a gas chromatograph, the sample vaporization chamber is kept at a temperature higher than the boiling point of the target component to be analyzed, and the injected liquid sample is vaporized therein and introduced into a column. The portion of the sample which remains at the tip of the syringe needle when the sample is injected is vaporized because the tip of the needle is heated, causing a change in the composition due to the phenomenon of discrimination. Because it is after the plunger is pushed and the sample is injected and until the syringe needle is pulled out of the sample vaporization chamber that the phenomenon of discrimination can take place, the effect of discrimination is reduced according to this invention by shortening this period. In other words, the syringe needle may be caused to penetrate the septum relatively slowly as long as the processes thereafter are carried out speedily in order to eliminate the ill-effects of discrimination.

The processes of a method embodying this invention are explained next with reference to drawings showing a syringe 2 provided with a plunger 3 and a needle 4. FIG. 1A shows that the plunger 3 has been retracted, say, by an automatic injector, and that a sample 6 has been sucked into the syringe 3 through the needle 4. The sample 6 is shown as filling the needle 4 to its tip. Air is thereafter introduced into the needle 4, as shown in FIG. 1B. The amount of air which is sucked in is slightly greater than the capacity of the needle 4. It may be normally about 0.5–1 μm although this depends on the kind of the syringe. The needle 4 is then caused to penetrate a septum 12 at the inlet to the sample vaporization chamber 10 so as to be inserted into the interior of the chamber 10, as shown in FIG. 1C. This process is carried out slowly, taking over a few hundred to several hundred milliseconds. Since there is no sample inside the needle 4 and air has been sucked in, there is no vaporization of sample from the tip of the needle 4 although the needle 4 passes through the septum 12 at a slow speed and the needle 4 is heated. In other words, the peak bandwidth of the gas chromatogram is not thereby increased. Numeral 14 indicates a column for analysis. Next, the plunger 3 of the syringe 2 is pushed to inject the sample sucked into the syringe 2 into the sample vaporization chamber 10, as shown in FIG. 1D. Thereafter, the needle 4 is pulled out of the sample vaporization chamber 10 to complete the injection. In the above, the processes shown in FIGS. 1D and 1E are carried out faster than the process shown in FIG. 1C.

According to the example described above, air is introduced into the needle 4 when the sample 6 is sucked into the syringe 2 such that the air is also injected into the sample vaporization chamber 10 together with the sample 6. By thus introducing air into the needle 4, it is possible to prevent vaporization of the sample from the tip of the needle although the needle 4 is being inserted into the sample vaporization chamber 10 at a slow speed and to thereby prevent the peak band width from widening. There are situations, however, where problems may occur if air is also injected into the sample vaporization chamber 10, such as when a thermal conductivity detector or an electrical conductivity detector is used as the detector because the introduction of air can affect the thermal or electrical conductivity. In such a situation, either a solvent, instead of air, is introduced into the needle 4, or the needle 4 is inserted into the sample vaporization chamber 10 while the sample is in the condition of filling the needle 4 to its tip. When the needle is filled with the sample to its tip, the peak width does not expand abnormally if the time required for the series of operations for injecting the sample is made equal to that by a prior art automatic injector. Although there is a possibility that components with low boiling points near the tip of the needle 4 may vaporize while the needle 4 is penetrating the septum 12 but the portion of the sample which vaporizes while the plunger 3 is being pushed and the sample is being injected into the sample vaporization chamber 10 is that which is intended to be pushed out by the plunger 3. It therefore does not cause a change in the composition due to discrimination.

In order to introduce air into the needle 4 after the sample is sucked into the syringe 2, the driving mechanism of the plunger 3 must be adjusted such that the plunger 3 can be further retracted after it is initially pulled backward to suck in the sample. It is preferable to provide a stepping motor for such a driving mechanism.

In summary, the process of inserting the syringe needle through the septum of the sample vaporization chamber is carried out slowly, taking longer than a few hundred to several hundred milliseconds (say, over 400 milliseconds), while the processes of pushing the plunger to inject the sample into the sample vaporization chamber and pulling the syringe needle out of the sample vaporization chamber are carried out sufficiently faster (say, less than 200 milliseconds) than the process of inserting the syringe needle into the septum. As a result, not only does it become possible to control the effects of changes in composition due to discrimination and to improve the accuracy of analysis and repeatability, but the load on the driving mechanism for driving the syringe can be made lighter because the insertion of the syringe needle is carried out slowly, reducing the possibility of causing the needle to become bent and the frequency of maintenance work for exchanging the needles.

What is claimed is:

1. A method of injecting a sample into a gas chromatograph, said method comprising:

a first process of causing a needle of a syringe, into which a sample has been introduced together with air so as to prevent vaporization of said sample through said needle into said sample vaporization chamber, to penetrate a septum and be inserted into a sample vaporization chamber, said first process being carried out over a period of over 400 milliseconds;

a second process of pushing a plunger to thereby cause said sample and said air inside said syringe to be injected together into said sample vaporization chamber; and a third process of pulling said needle out of said sample vaporization chamber, said second process and said third process being carried out within a period of less than 200 milliseconds.

2. A method of injecting a sample into a gas chromatograph, said method comprising:

a first process of causing a needle of a syringe, into which a sample has been introduced together with a solvent so as to prevent vaporization of said sample through said needle into said sample vaporization chamber, to penetrate a septum and be inserted into a sample vaporization chamber, said first process being carried out over a period of over 400 milliseconds;

second process of pushing a plunger to thereby cause said sample and said solvent inside said syringe to be injected together into said sample vaporization chamber; and a third process of pulling said needle out of said sample vaporization chamber, said second process and said third process being carried out within a period of less than 200 milliseconds.

* * * * *